US011112401B2

(12) United States Patent
Tasker

(10) Patent No.: US 11,112,401 B2
(45) Date of Patent: Sep. 7, 2021

(54) METHOD FOR DETERMINING THE CELL MEDIATED IMMUNE COMPETENCE OF A SUBJECT

(71) Applicant: Oxford Immunotec Limited, Oxfordshire (GB)

(72) Inventor: Scott Tasker, London (GB)

(73) Assignee: Oxford Immunotec Limited, Oxfordshire (GB)

(*) Notice: Subject to any disclaimer, the term of this patent is extended or adjusted under 35 U.S.C. 154(b) by 0 days.

(21) Appl. No.: 16/086,811

(22) PCT Filed: Mar. 27, 2017

(86) PCT No.: PCT/GB2017/050855
§ 371 (c)(1),
(2) Date: Sep. 20, 2018

(87) PCT Pub. No.: WO2017/168135
PCT Pub. Date: Oct. 5, 2017

(65) Prior Publication Data
US 2019/0064145 A1 Feb. 28, 2019

(30) Foreign Application Priority Data
Mar. 29, 2016 (GB) .................................... 1605210

(51) Int. Cl.
*G01N 33/50* (2006.01)
*C07K 7/08* (2006.01)
*C40B 40/08* (2006.01)
*G01N 33/569* (2006.01)

(52) U.S. Cl.
CPC .......... *G01N 33/505* (2013.01); *C07K 7/08* (2013.01); *C40B 40/08* (2013.01); *G01N 33/5047* (2013.01); *G01N 33/5052* (2013.01); *G01N 33/56983* (2013.01)

(58) Field of Classification Search
None
See application file for complete search history.

(56) References Cited

U.S. PATENT DOCUMENTS

| | | | |
|---|---|---|---|
| 2005/0249744 A1* | 11/2005 | Van Els | C07K 14/005 424/186.1 |
| 2009/0062237 A1 | 3/2009 | Abraham et al. | |
| 2009/0304735 A1 | 12/2009 | Belz et al. | |
| 2013/0164315 A1 | 6/2013 | Lambkin-Williams et al. | |
| 2015/0023996 A1 | 1/2015 | Lee et al. | |

FOREIGN PATENT DOCUMENTS

| | | |
|---|---|---|
| CN | 101489589 A | 7/2009 |
| JP | 2015-506179 A | 3/2015 |
| WO | WO-2007/106939 A1 | 9/2007 |
| WO | WO-2013/172926 A1 | 11/2013 |
| WO | WO-2013172926 A1 * | 11/2013 ......... G01N 33/6854 |
| WO | WO-2014/100853 A1 | 7/2014 |
| WO | WO-2017/168135 A1 | 10/2017 |

OTHER PUBLICATIONS

Roederer et al., J Imunno Methods vol. 274, pp. 221-228 (Year: 2003).*
AnaSpec: Product Information Sheet, CEF Control Peptide Pool, Catalog No. AS-61036-003, Nov. 23, 2013, Retrieved from: <<URL:https://www.anaspec.com/products/product.asp?id=45991 &productid=27088>>. Accessed on May 4, 2017.
Cox, J. H. and Hayes, P., Qualification and Use of Peptide Libraries for Clinical Trial Immunomonitoring, JPT Peptide Technologies, Jan. 1, 2013, Retrieved from: <<https://www.jpt.com/fileadmin/useruplcad/NEW/Products_Services/Products/PepMix_TM_Peptide_Pools/AppNote_PepTrack_Pe pMix-1301_01.pdf<<. Accessed on May 4, 2017.
Currier, J. R. et al, A panel of MHC class I restricted viral peptides for use as a quality control for vaccine ELISPOT assays, Journal of Immunological Methods, 260:157-172 (2002).
International Search Report for PCT/GB2017/050855 (Method for Determining the Cell Mediated Immune Competence of a Subject, filed Mar. 27, 2017), issued by ISA/EPO, 6 pages (May 15, 2017).
Kern, F., Cytomegalovirus Protein Spanning PepMix™ Peptide Pools to Discover Changes in T-Cell Immunity in the Aging Population, JPT Peptide Technologies, Mar. 2012, Retrieved from: <<https://www.jpt.com/fileadmin/user uplcad/NEW/ProductsServices/Products/PepMix_TM_Peptide_Pools/AppNote_HCMV_1203.pdf>>. Accessed on May 4, 2017.
Lipschultz, S. E. et al, Issues in solid-organ transplantation in children: translational research from bench to bedside, Clinics, 69(S1): 55-72 (2014).
Mangi, R. J. and Kantor, F. S., The Multiple Mixed Lymphocyte Reaction: Variables Important in the Test as a Measure of Lymphocyte Competence in Man, The Yale Journal of Biology and Medicine, 48: 217-228 (1975).
Mézière, C. et al, In Vivo T Helper Cell Response to Retro-Inverso Peptidomimetics, The Journal of Immunology, 159(7): 3230-3237 (1997).
PepMix CEF Pool (extended) (120nmol) (>70%), Product Code: PM-CEF-E-2, Product Data Sheet, JPT Innovative Peptide Solutions, Mar. 1, 2012, Retrieved from: <<https://shop.jpt.com/images/upload/pdf/Datasheet CEF Pool (extended) 120-70.pdf>>. Accessed on May 4, 2017.

(Continued)

*Primary Examiner* — Shanon A. Foley
*Assistant Examiner* — Myron G Hill
(74) *Attorney, Agent, or Firm* — Choate, Hall & Stewart LLP; Charles E. Lyon; Brian E. Reese

(57) ABSTRACT

The invention relates to a method for determining the cell mediated immune competence of a subject. The method comprises conducting a cell-mediated immunoassay (CMI) on a sample comprising immune cells from a subject. The method further comprises detecting in vitro an immune response to a pool of peptides, wherein the pool of peptides is derived from at least three viral antigens.

16 Claims, 4 Drawing Sheets

Specification includes a Sequence Listing.

(56) References Cited

OTHER PUBLICATIONS

PepMix™ Peptide Pools, JPT Innovative Peptide Pools, Mar. 22, 2016, Retrieved from <<https://www.jpt.com/products/pepmix-peptide-pools/>>. Accessed on May 4, 2017.

Roederer, M. and Koup, R. A., Optimized determination of T cell epitope responses, Journal of Immunological Methods, 274: 221-228 (2003).

Written Opinion for PCT/GB2017/050855 (Method for Determining the Cell Mediated Immune Competence of a Subject, filed Mar. 27, 2017), issued by ISA/EPO, 7 pages (May 15, 2017).

* cited by examiner

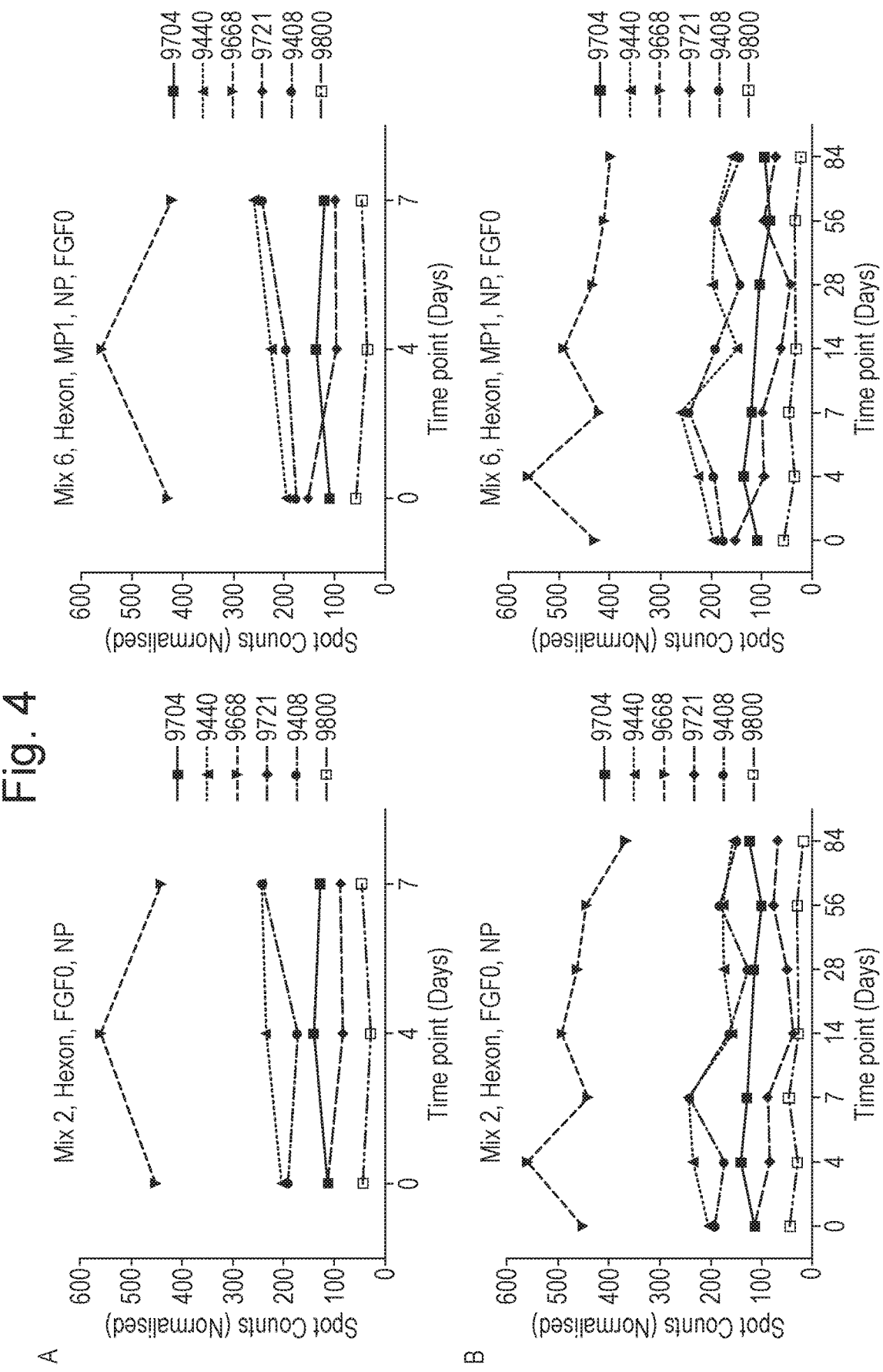

SEQUENCE LISTING

<160> NUMBER OF SEQ ID NOS: 31

<210> SEQ ID NO 1
<211> LENGTH: 9
<212> TYPE: PRT
<213> ORGANISM: Epstein Barr Virus

<400> SEQUENCE: 1

Phe Leu Asp Lys Gly Thr Tyr Thr Leu
1               5

<210> SEQ ID NO 2
<211> LENGTH: 9
<212> TYPE: PRT
<213> ORGANISM: Epstein Barr Virus

<400> SEQUENCE: 2

Gly Leu Cys Thr Leu Val Ala Met Leu
1               5

<210> SEQ ID NO 3
<211> LENGTH: 10
<212> TYPE: PRT
<213> ORGANISM: Epstein Barr Virus

<400> SEQUENCE: 3

Asp Tyr Cys Asn Val Leu Asn Lys Glu Phe
1               5                   10

<210> SEQ ID NO 4
<211> LENGTH: 9
<212> TYPE: PRT
<213> ORGANISM: Epstein Barr Virus

<400> SEQUENCE: 4

Ala Thr Ile Gly Thr Ala Met Tyr Lys
1               5

<210> SEQ ID NO 5
<211> LENGTH: 9
<212> TYPE: PRT
<213> ORGANISM: Epstein Barr Virus

<400> SEQUENCE: 5

Arg Val Arg Ala Tyr Thr Tyr Ser Lys
1               5

<210> SEQ ID NO 6
<211> LENGTH: 8
<212> TYPE: PRT

<213> ORGANISM: Epstein Barr Virus

<400> SEQUENCE: 6

Arg Ala Lys Phe Lys Gln Leu Leu
1               5

<210> SEQ ID NO 7
<211> LENGTH: 11
<212> TYPE: PRT
<213> ORGANISM: Epstein Barr Virus

<400> SEQUENCE: 7

Glu Pro Leu Pro Gln Gly Gln Leu Thr Ala Tyr
1               5                   10

<210> SEQ ID NO 8
<211> LENGTH: 11
<212> TYPE: PRT
<213> ORGANISM: Epstein Barr Virus

<400> SEQUENCE: 8

His Pro Val Gly Glu Ala Asp Tyr Phe Glu Tyr
1               5                   10

<210> SEQ ID NO 9
<211> LENGTH: 9
<212> TYPE: PRT
<213> ORGANISM: Epstein Barr Virus

<400> SEQUENCE: 9

Gln Ala Lys Trp Arg Leu Gln Thr Leu
1               5

<210> SEQ ID NO 10
<211> LENGTH: 9
<212> TYPE: PRT
<213> ORGANISM: Epstein Barr Virus

<400> SEQUENCE: 10

Phe Leu Arg Gly Arg Ala Tyr Gly Leu
1               5

<210> SEQ ID NO 11
<211> LENGTH: 9
<212> TYPE: PRT
<213> ORGANISM: Epstein Barr Virus

<400> SEQUENCE: 11

Arg Pro Pro Ile Phe Ile Arg Arg Leu
1               5

<210> SEQ ID NO 12
<211> LENGTH: 9
<212> TYPE: PRT
<213> ORGANISM: Epstein Barr Virus

<400> SEQUENCE: 12

Tyr Pro Leu His Glu Gln His Gly Met
1               5

<210> SEQ ID NO 13
<211> LENGTH: 9
<212> TYPE: PRT
<213> ORGANISM: Epstein Barr Virus

```
<400> SEQUENCE: 13

Arg Leu Arg Ala Glu Ala Gln Val Lys
1               5

<210> SEQ ID NO 14
<211> LENGTH: 10
<212> TYPE: PRT
<213> ORGANISM: Epstein Barr Virus

<400> SEQUENCE: 14

Ala Val Phe Asp Arg Lys Ser Asp Ala Lys
1               5                   10

<210> SEQ ID NO 15
<211> LENGTH: 9
<212> TYPE: PRT
<213> ORGANISM: Epstein Barr Virus

<400> SEQUENCE: 15

Arg Arg Ile Tyr Asp Leu Ile Glu Leu
1               5

<210> SEQ ID NO 16
<211> LENGTH: 10
<212> TYPE: PRT
<213> ORGANISM: Epstein Barr Virus

<400> SEQUENCE: 16

Glu Glu Asn Leu Leu Asp Phe Val Arg Phe
1               5                   10

<210> SEQ ID NO 17
<211> LENGTH: 9
<212> TYPE: PRT
<213> ORGANISM: Epstein Barr Virus

<400> SEQUENCE: 17

Gln Pro Arg Ala Pro Ile Arg Pro Ile
1               5

<210> SEQ ID NO 18
<211> LENGTH: 9
<212> TYPE: PRT
<213> ORGANISM: Epstein Barr Virus

<400> SEQUENCE: 18

Ile Val Thr Asp Phe Ser Val Ile Lys
1               5

<210> SEQ ID NO 19
<211> LENGTH: 9
<212> TYPE: PRT
<213> ORGANISM: Epstein Barr Virus

<400> SEQUENCE: 19

Tyr Leu Leu Glu Met Leu Trp Arg Leu
1               5

<210> SEQ ID NO 20
<211> LENGTH: 9
<212> TYPE: PRT
<213> ORGANISM: Epstein Barr Virus

<400> SEQUENCE: 20
```

```
Pro Tyr Leu Phe Trp Leu Ala Ala Ile
1               5

<210> SEQ ID NO 21
<211> LENGTH: 9
<212> TYPE: PRT
<213> ORGANISM: Epstein Barr Virus

<400> SEQUENCE: 21

Ile Glu Asp Pro Phe Asn Ser Leu
1               5

<210> SEQ ID NO 22
<211> LENGTH: 10
<212> TYPE: PRT
<213> ORGANISM: Epstein Barr Virus

<400> SEQUENCE: 22

Ser Ser Cys Ser Ser Cys Pro Leu Ser Lys
1               5                   10

<210> SEQ ID NO 23
<211> LENGTH: 9
<212> TYPE: PRT
<213> ORGANISM: Epstein Barr Virus

<400> SEQUENCE: 23

Phe Leu Tyr Ala Leu Ala Leu Leu Leu
1               5

<210> SEQ ID NO 24
<211> LENGTH: 9
<212> TYPE: PRT
<213> ORGANISM: Epstein Barr Virus

<400> SEQUENCE: 24

Thr Tyr Gly Pro Val Phe Met Cys Leu
1               5

<210> SEQ ID NO 25
<211> LENGTH: 9
<212> TYPE: PRT
<213> ORGANISM: Epstein Barr Virus

<400> SEQUENCE: 25

Thr Tyr Gly Pro Val Phe Met Ser Leu
1               5

<210> SEQ ID NO 26
<211> LENGTH: 9
<212> TYPE: PRT
<213> ORGANISM: Epstein Barr Virus

<400> SEQUENCE: 26

Cys Leu Gly Gly Leu Leu Thr Met Val
1               5

<210> SEQ ID NO 27
<211> LENGTH: 245
<212> TYPE: PRT
<213> ORGANISM: Epstein Barr Virus

<400> SEQUENCE: 27

Met Met Asp Pro Asn Ser Thr Ser Glu Asp Val Lys Phe Thr Pro Asp
1               5                   10                  15
```

```
Pro Tyr Gln Val Pro Phe Val Gln Ala Phe Asp Gln Ala Thr Arg Val
            20                  25                  30

Tyr Gln Asp Leu Gly Gly Pro Ser Gln Ala Pro Leu Pro Cys Val Leu
        35                  40                  45

Trp Pro Val Leu Pro Glu Pro Leu Pro Gln Gly Gln Leu Thr Ala Tyr
 50                  55                  60

His Val Ser Thr Ala Pro Thr Gly Ser Trp Phe Ser Ala Pro Gln Pro
 65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Lys Gln Met Cys Pro Ser
            210                 215                 220

Leu Asp Val Asp Ser Ile Ile Pro Arg Thr Pro Asp Val Leu His Glu
225                 230                 235                 240

Asp Leu Leu Asn Phe
            245

<210> SEQ ID NO 28
<211> LENGTH: 944
<212> TYPE: PRT
<213> ORGANISM: Human Adenovirus 3

<400> SEQUENCE: 28

Met Ala Thr Pro Ser Met Met Pro Gln Trp Ala Tyr Met His Ile Ala
 1               5                  10                  15

Gly Gln Asp Ala Ser Gly Tyr Leu Ser Pro Gly Leu Val Gln Phe Ala
            20                  25                  30

Arg Ala Thr Asp Thr Tyr Phe Ser Met Gly Asn Lys Phe Arg Asn Pro
        35                  40                  45

Thr Val Ala Pro Thr His Asp Val Thr Thr Asp Arg Ser Gln Arg Leu
 50                  55                  60

Met Leu Arg Phe Val Pro Val Asp Arg Glu Asp Asn Thr Tyr Ser Tyr
 65                  70                  75                  80

Lys Val Arg Tyr Thr Leu Ala Val Gly Asp Asn Arg Val Leu Asp Met
                85                  90                  95

Ala Ser Thr Phe Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Ser Gln Trp Ile Val Thr Thr Asn Gly Asp Asn Ala
```

```
            130                 135                 140
Val Thr Thr Thr Thr Asn Thr Phe Gly Ile Ala Ser Met Lys Gly Gly
145                 150                 155                 160

Asn Ile Thr Lys Glu Gly Leu Gln Ile Gly Lys Asp Ile Thr Thr Thr
                165                 170                 175

Glu Gly Glu Glu Lys Pro Ile Tyr Ala Asp Lys Thr Tyr Gln Pro Glu
            180                 185                 190

Pro Gln Val Gly Glu Glu Ser Trp Thr Asp Thr Asp Gly Thr Asn Glu
                195                 200                 205

Lys Phe Gly Gly Arg Ala Leu Lys Pro Ala Thr Asn Met Lys Pro Cys
210                 215                 220

Tyr Gly Ser Phe Ala Arg Pro Thr Asn Ile Lys Gly Gly Gln Ala Lys
225                 230                 235                 240

Asn Arg Lys Val Lys Pro Thr Thr Glu Gly Gly Val Glu Thr Glu Glu
                245                 250                 255

Pro Asp Ile Asp Met Glu Phe Phe Asp Gly Arg Asp Ala Val Ala Gly
            260                 265                 270

Ala Leu Ala Pro Glu Ile Val Leu Tyr Thr Glu Asn Val Asn Leu Glu
        275                 280                 285

Thr Pro Asp Ser His Val Val Tyr Lys Pro Glu Thr Ser Asn Asn Ser
290                 295                 300

His Ala Asn Leu Gly Gln Gln Ala Met Pro Asn Arg Pro Asn Tyr Ile
305                 310                 315                 320

Gly Phe Arg Asp Asn Phe Val Gly Leu Met Tyr Tyr Asn Ser Thr Gly
                325                 330                 335

Asn Met Gly Val Leu Ala Gly Gln Ala Ser Gln Leu Asn Ala Val Val
            340                 345                 350

Asp Leu Gln Asp Arg Asn Thr Glu Leu Ser Tyr Gln Leu Leu Leu Asp
        355                 360                 365

Ser Leu Gly Asp Arg Thr Arg Tyr Phe Ser Met Trp Asn Gln Ala Val
370                 375                 380

Asp Ser Tyr Asp Pro Asp Val Arg Ile Ile Glu Asn His Gly Ile Glu
385                 390                 395                 400

Asp Glu Leu Pro Asn Tyr Cys Phe Pro Leu Asn Gly Ile Gly Pro Gly
                405                 410                 415

His Thr Tyr Gln Gly Ile Lys Val Lys Thr Asp Thr Asn Gly Trp
            420                 425                 430

Glu Lys Asp Ala Asn Val Ala Pro Ala Asn Glu Ile Thr Ile Gly Asn
        435                 440                 445

Asn Leu Ala Met Glu Ile Asn Ile Gln Ala Asn Leu Trp Arg Ser Phe
450                 455                 460

Leu Tyr Ser Asn Val Ala Leu Tyr Leu Pro Asp Val Tyr Lys Tyr Thr
465                 470                 475                 480

Pro Pro Asn Ile Thr Leu Pro Thr Asn Thr Asn Thr Tyr Glu Tyr Met
                485                 490                 495

Asn Gly Arg Val Val Ser Pro Ser Leu Val Asp Ser Tyr Ile Asn Ile
            500                 505                 510

Gly Ala Arg Trp Ser Leu Asp Pro Met Asp Asn Val Asn Pro Phe Asn
        515                 520                 525

His His Arg Asn Ala Gly Leu Arg Tyr Arg Ser Met Leu Leu Gly Asn
530                 535                 540

Gly Arg Tyr Val Pro Phe His Ile Gln Val Pro Gln Lys Phe Phe Ala
545                 550                 555                 560
```

-continued

Val Lys Asn Leu Leu Leu Pro Gly Ser Tyr Thr Tyr Glu Trp Asn
            565                 570                 575

Phe Arg Lys Asp Val Asn Met Val Leu Gln Ser Ser Leu Gly Asn Asp
        580                 585                 590

Leu Arg Thr Asp Gly Ala Thr Ile Ser Phe Thr Ser Ile Asn Leu Tyr
        595                 600                 605

Ala Thr Phe Phe Pro Met Ala His Asn Thr Ala Ser Thr Leu Glu Ala
        610                 615                 620

Met Leu Arg Asn Asp Thr Asn Asp Gln Ser Phe Asn Asp Tyr Leu Ser
625                 630                 635                 640

Ala Ala Asn Met Leu Tyr Pro Ile Pro Ala Asn Ala Thr Asn Ile Pro
            645                 650                 655

Ile Ser Ile Pro Ser Arg Asn Trp Ala Ala Phe Arg Gly Trp Ser Phe
            660                 665                 670

Thr Arg Leu Lys Thr Lys Glu Thr Pro Ser Leu Gly Ser Gly Phe Asp
            675                 680                 685

Pro Tyr Phe Val Tyr Ser Gly Ser Ile Pro Tyr Leu Asp Gly Thr Phe
            690                 695                 700

Tyr Leu Asn His Thr Phe Lys Lys Val Ala Ile Met Phe Asp Ser Ser
705                 710                 715                 720

Val Ser Trp Pro Gly Asn Asp Arg Leu Leu Ser Pro Asn Glu Phe Glu
                725                 730                 735

Ile Lys Arg Thr Val Asp Gly Glu Gly Tyr Asn Val Ala Gln Cys Asn
                740                 745                 750

Met Thr Lys Asp Trp Phe Leu Val Gln Met Leu Ala Asn Tyr Asn Ile
            755                 760                 765

Gly Tyr Gln Gly Phe Tyr Ile Pro Glu Gly Tyr Lys Asp Arg Met Tyr
            770                 775                 780

Ser Phe Phe Arg Asn Phe Gln Pro Met Ser Arg Gln Val Val Asp Glu
785                 790                 795                 800

Val Asn Tyr Thr Asp Tyr Lys Ala Val Thr Leu Pro Tyr Gln His Asn
                805                 810                 815

Asn Ser Gly Phe Val Gly Tyr Leu Ala Pro Thr Met Arg Gln Gly Glu
                820                 825                 830

Pro Tyr Pro Ala Asn Tyr Pro Tyr Pro Leu Ile Gly Thr Thr Ala Val
            835                 840                 845

Lys Ser Val Thr Gln Lys Lys Phe Leu Cys Asp Arg Thr Met Trp Arg
850                 855                 860

Ile Pro Phe Ser Ser Asn Phe Met Ser Met Gly Ala Leu Thr Asp Leu
865                 870                 875                 880

Gly Gln Asn Met Leu Tyr Ala Asn Ser Ala His Ala Leu Asp Met Thr
                885                 890                 895

Phe Glu Val Asp Pro Met Asp Glu Pro Thr Leu Leu Tyr Leu Leu Phe
                900                 905                 910

Glu Val Phe Asp Val Val Arg Val His Gln Pro His Arg Gly Val Ile
            915                 920                 925

Glu Ala Val Tyr Leu Arg Thr Pro Phe Ser Ala Gly Asn Ala Thr Thr
            930                 935                 940

<210> SEQ ID NO 29
<211> LENGTH: 498
<212> TYPE: PRT
<213> ORGANISM: Influenza A Virus

<400> SEQUENCE: 29

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Arg Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Ser Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
        275                 280                 285

Tyr Asn Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Val Gln Ile Ala Ser Asn
        355                 360                 365

Glu Asn Met Asp Asn Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415
```

```
Asn Leu Pro Phe Glu Lys Ser Thr Val Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 30
<211> LENGTH: 574
<212> TYPE: PRT
<213> ORGANISM: Human Respiratory Syncytial Virus B

<400> SEQUENCE: 30

Met Glu Leu Leu Ile His Arg Leu Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Phe Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Ala Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Asn Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asn Asn Gln Leu Leu Pro Ile Val Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Asn Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285
```

```
Met Ser Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Thr Ile Ile Ile Val Ile Ile Val Val Leu Leu Ser Leu Ile Ala Ile
530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 31
<211> LENGTH: 252
<212> TYPE: PRT
<213> ORGANISM: Influenza A Virus

<400> SEQUENCE: 31

Met Ser Leu Leu Thr Glu Val Glu Thr Tyr Val Leu Ser Ile Val Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
50                  55                  60

Thr Leu Thr Cys Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
```

-continued

```
            85                  90                  95
Val Lys Leu Tyr Arg Lys Leu Lys Arg Glu Ile Thr Phe His Gly Ala
                100                 105                 110

Lys Glu Ile Ala Leu Ser Tyr Ser Ala Gly Ala Leu Ala Ser Cys Met
            115                 120                 125

Gly Leu Ile Tyr Asn Arg Met Gly Ala Val Thr Thr Glu Val Ala Phe
            130                 135                 140

Gly Leu Val Cys Ala Thr Cys Glu Gln Ile Ala Asp Ser Gln His Arg
145                 150                 155                 160

Ser His Arg Gln Met Val Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
            195                 200                 205

Ala Arg Gln Met Val Gln Ala Met Arg Ala Ile Gly Thr His Pro Arg
            210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250
```

METHOD FOR DETERMINING THE CELL MEDIATED IMMUNE COMPETENCE OF A SUBJECT

FIELD OF THE INVENTION

The present invention relates to a method for determining the cell mediated immune competence of a subject. In particular, the method comprises conducting a cell mediated immunoassay on a sample comprising immune cells, for example peripheral blood mononuclear cells (PBMCs) obtained from the subject and detecting an immune response to at least three viral antigens.

BACKGROUND

Immune competence relates to the presence of a normally functioning immune response in an individual including adaptive (T cells and B cells) and innate (complement and toll-like receptor) immune responses. Assays designed to measure immune competence, in particular cell mediated immune competence, can be used to monitor the T cell response of a donor to an antigen. It is desirable to measure or monitor the immune competence in an individual, and in particular their general ability to mount a cell mediated immune response. For example, an assessment of immune competence is of use to clinicians for several disease conditions including transplantation, cancer, autoimmune diseases, HIV and vaccine trials.

Assays which provide a measure of immune functionality, include commercially available products Cylex Immunknow and QFT Monitor®. The Mixed Lymphocyte Reaction (MLR) can also be used to assess the immune response in an individual.

Cylex Immunknow measures ATP production from whole blood following stimulation with PHA. This relies on non-specific stimulation of the cells contained in the blood sample. The effectiveness of this assay for measuring immune functionality has received mixed results (Lipschultz et al. (2014))

Quantiferon Monitor® provides both a qualitative and quantitative measure of immune function (Quantiferon Monitor® Pack Insert 2014). In particular, the QFM involves stimulating whole blood with a combination of innate (TLR mediated)+adaptive (TCR mediated) antigens. IFNγ secreted from cells responding to the antigens is detected by ELISA. The QFM readout puts donors into 3 categories: Low (<15 IU/mL IFNγ), Medium (15-1000 IU/mL IFNγ) and High (IU/mL IFNγ).

The Mixed Lymphocyte Reaction (MLR) assay has been used within the research community as a predictor of T cell functionality (Manji et al. (1975)). In particular the MLR assay involves mixing a sample of PBMCs with PBMCs from control (treated to prevent proliferation), adding a radio dye and measuring proliferation of sample PBMCs by decay of radio dye.

SUMMARY OF INVENTION

The present inventors have identified that the cell mediated immune competence of an individual can be determined by using a selection of viral antigens. By selecting an appropriate pool of viral antigens, the immune competence of a wide range of individuals can be determined, allowing a single assay system to be developed for testing the immune competence of a wide range of individuals.

In accordance with the present invention, there is provided a method for determining the cell mediated immune competence of a subject, wherein the method comprises conducting a cell-mediated immunoassay (CMI) on a sample comprising immune cells, for example peripheral blood mononuclear cells (PBMCs) from the subject, the method comprising detecting in vitro an immune response to a pool of peptides, wherein the pool of peptides is derived from at least three viral antigens.

A method according to claim 1, wherein the pool or peptides is derived from at least four, five or six viral antigens.

In a preferred embodiment, the pool of peptides is derived from three, four or five viral antigens.

In one aspect, the viral antigens are selected from the hexon protein of human adenovirus 3, the matrix protein 1 (H3N2) of the influenza virus, the BZLF-1 protein of the Epstein Barr virus, the nucleocapsid protein of the influenza virus, the fusion glycoprotein G0 of the respiratory syncytial virus.

In one aspect of the invention, the viral antigens consist of the hexon protein of human adenovirus 3, the fusion glycoprotein G0 of the respiratory syncytial virus and the nucleocapsid protein of the influenza virus.

In another aspect of the invention, the viral antigens consist of the hexon protein of human adenovirus 3, the matrix protein 1 of the influenza virus, the nucleocapsid protein of the influenza virus and the fusion glycoprotein G0 of the respiratory syncytial virus.

In a further aspect of the invention, the viral antigens consist of the hexon protein of human adenovirus 3, the trans-activator protein BZLF1 of the Epstein Barr virus and the fusion glycoprotein G0 of the respiratory syncytial virus.

In a further aspect of the invention, the viral antigens consist of the hexon protein of human adenovirus 3, the BALF-4, BMLF-1, BRLF-1, BZLF-1 EBNA-1, EBNA-3A, EBNA-3B, EBNA-3C, EBNA-4, LMP-1 and LMP-2 proteins of the Epstein Barr virus, the matrix protein 1 of the influenza virus, the nucleocapsid protein of the influenza virus and the fusion glycoprotein G0 of the respiratory syncytial virus.

BRIEF DESCRIPTION OF THE DRAWINGS

FIG. 4. Example graphs showing the testing of the variation of responses in immune competent donors using ICA Mixes in an ELISPOT assay.

DETAILED DESCRIPTION OF THE INVENTION

Figure 1:
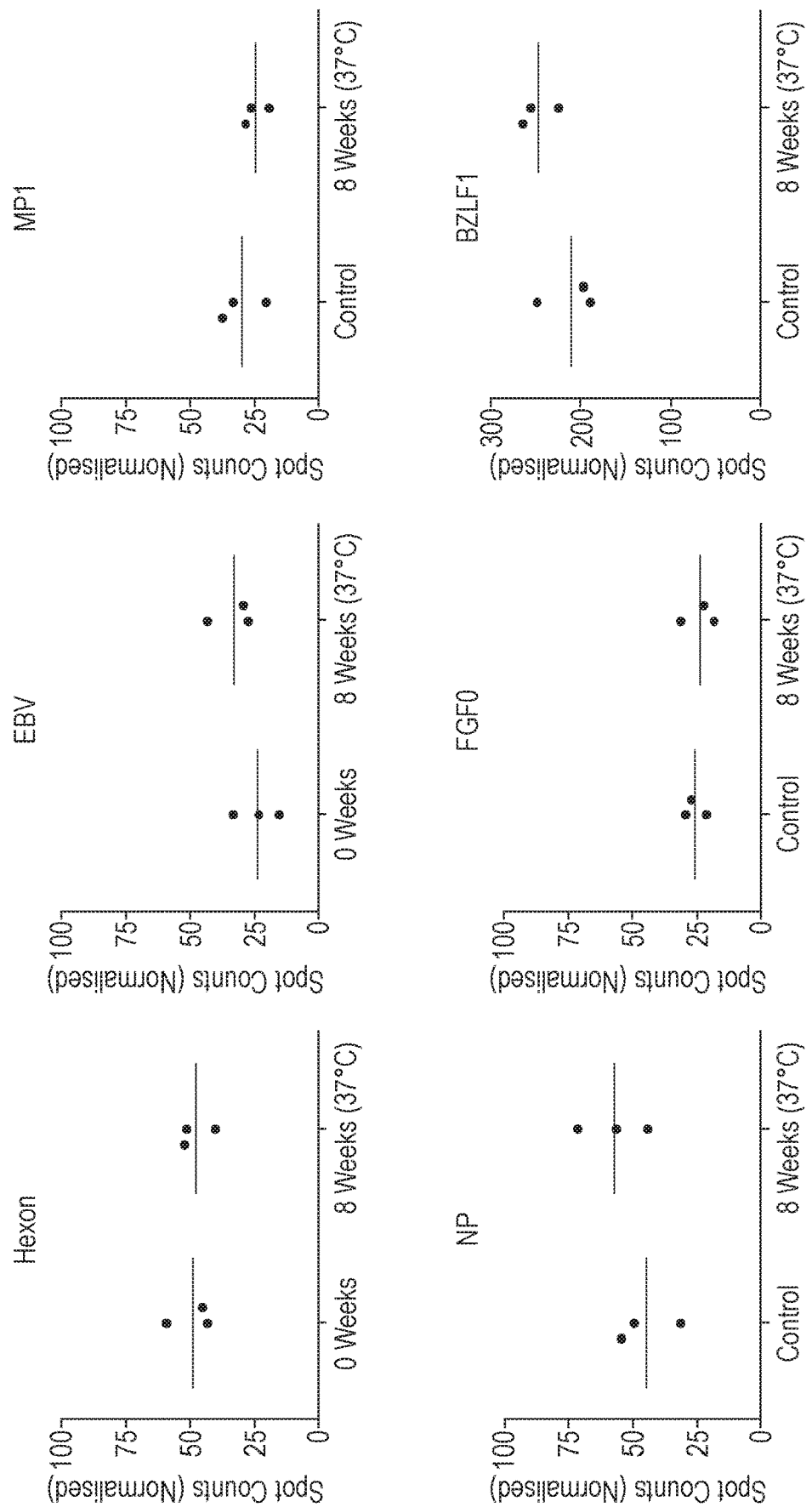
FIG. 1. Example graphs for accelerated stability testing of Hexon, EBV, MP1, NP, FGF0 and BZLF1 in an ELISPOT assay.

It is to be understood that different applications of the disclosed methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a fragment" includes "fragments", reference to "a cell" includes two or more such cells, reference to "a subject" includes two or more such subjects, and the like.

All publications, patents and patent applications cited herein, whether supra or infra, are hereby incorporated by reference in their entirety.

Methods of the Invention

The present inventors have identified a method of determining immune competence of a subject using a cell mediated immunoassay (CMI assay). A CMI assay designed to measure immune competence, in particular cell mediated immune competence, can be used to monitor the T cell response of a donor to antigen. The inventors have identified that an appropriate pool of viral antigens can be selected for the detection of a cell mediated immune response in a wide variety of individuals. The pool of viral antigens provides a response in immune competent individuals, regardless of their background. Thus, the assay can be used to identify immunocompetent individuals, and also those individual who can not mount an effect immune response.

Accordingly, the present invention provides for a method of determining immune competence of a subject, wherein the method comprises conducting a cell mediated immunoassay (CMI) on a sample comprising immune cells, for example peripheral blood mononuclear cells (PBMCs) from the subject, the method comprising detecting in vitro an immune response to a pool of peptides, wherein the pool of peptides is derived from at least three viral antigens.

The method may comprise a pool of peptides derived from at least three, at least four, at least five, or at least six viral antigens, up to seven or eight viral antigens.

In a particularly preferred embodiment, the peptides are derived from three, four, five or six viral antigens. In a particularly preferred embodiment, the peptides are derived from three, four or five (but not more) viral antigens. In an alternative aspect of the invention, the peptides are derived from two, three or four viral antigens and additionally comprise a pool of antigens derived from EBV, but do not comprise any other viral antigens.

The pool of peptides may comprise peptides derived from viral antigens of a single virus, more than one virus, or all from different viruses. The pool of peptides may comprise peptides derived from viral antigens of the same virus and of different viruses. In a preferred aspect of the invention, the at least three viral antigens are derived from at least two viruses, preferably from three, four, five or six viruses. In a preferred embodiment, the at least three viral antigens are derived from one or more of the human adenovirus 3, the influenza virus, the Epstein Barr virus and the respiratory syncytial virus.

In a more preferred embodiment, the viral antigens are selected from the hexon protein derived from the human adenovirus 3, the matrix protein 1 derived from the influenza virus, the nucleocapsid protein derived from the influenza virus, the BZLF-1 protein derived from the Epstein Barr virus and the fusion glycoprotein G0 derived from the respiratory syncytial virus. The influenza virus can be any influenza strain. In a particularly preferred embodiment, the influenza virus is influenza strain H3N2.

In one embodiment of the invention, the pool of viral antigens consist of the hexon protein of human adenovirus 3, the fusion glycoprotein G0 of the respiratory syncytial virus and the nucleocapsid protein of the influenza virus.

In another embodiment of the invention, the pool of viral antigens consist of the hexon protein of human adenovirus 3, the matrix protein 1 of the influenza virus, the nucleocapsid protein of the influenza virus and the fusion glycoprotein G0 of the respiratory syncytial virus.

In a further embodiment of the invention, the pool of viral antigens consist of the hexon protein of human adenovirus 3, the trans-activator protein BZLF1 of the Epstein Barr virus and the fusion glycoprotein G0 of the respiratory syncytial virus.

In another preferred embodiment, one or more of the viral antigens are derived from Epstein Barr virus, wherein the viral antigens comprise one or more of the BALF-4, BMLF-1, BRLF-1, BZLF-1 EBNA-1, EBNA-3A, EBNA-3B, EBNA-3C, EBNA-4, LMP-1 and LMP-2 proteins. In a particularly preferred embodiment, a pool of peptides derived from EBV is provided, the pool of peptides including peptides derived from each of the BALF-4, BMLF-1, BRLF-1, BZLF-1 EBNA-1, EBNA-3A, EBNA-3B, EBNA-3C, EBNA-4, LMP-1 and LMP-2 proteins. Such a pool of EBV peptides may be provided in combination with the hexon protein of human adenovirus 3, the matrix protein 1 of the influenza virus, the nucleocapsid protein of the influenza virus and the fusion glycoprotein G0 of the respiratory syncytial virus.

Assays for CMI Responses

Cell Mediated Immune (CMI) responses are used to define the immune status of an individual. Typically, in the art of clinical immunology, the term CMI response encompasses skin testing, lymphocyte proliferation assays, and the detection of cytokines produced by immune cells, for example peripheral blood mononuclear cells (PBMC) in the presence of a specific antigen. The method of the present invention may comprise detecting an in vitro cell mediated immune response. In particular, the in vitro cytokine-based CMI response to peptides may be detected in the method of the present invention.

The cells of the immune system are capable of producing immune effector molecules such as cytokines following stimulation by antigen. CMI Assays involve incubating a cell sample with antigen and measuring for the presence (or absence) or quantity of an immune effector molecule such as a cytokine to provide an indication of the ability of the individual to generate a cell mediated immune response to the selected antigens. Cells for use in a CMI Assay may include a whole blood sample, a sample comprising immune cells, for example peripheral blood mononuclear cells (PMBCs) and isolated populations of lymphocytes (particularly T-cells) and antigen presenting cells (APCs). APCs are involved in processing the antigen in order that the antigen may be recognised by T-cell receptors on the surface of each T-cell. Antigen recognition may induce cytokine production.

Cells producing cytokines may be identified by flow cytometry. Flow cytometry may be used to quantify the frequency of cytokine producing cells, and/or the amount of cytokine production by the cells. Antigen-induced cytokines may be released into the assay medium and detected directly by, for example, ELISA methods, or quantified in terms of the frequency of cytokine-secreting T-cells using an enzyme-linked immunospot assay (ELISPOT). The method of the invention preferably comprises an ELISPOT.

The enzyme-linked immunospot assay (ELISPOT), otherwise known as the filter immunoplaque assay, was initially developed to detect and quantitate individual antibody-secreting B cells. At the time it was developed, the technique provided a rapid and versatile alternative to conventional plaque-forming cell assays. Recent modifications have improved the sensitivity of the ELISPOT such that cells producing as few as 100 molecules of a specific protein per second can be detected. This makes ELISPOT assays much more sensitive than conventional ELISA assays. ELISPOT assays take advantage of the relatively high concentration of a given proteinaceous cell product (such as a cytokine) in the environment immediately surrounding the protein-secreting cell. These cell products are captured and detected using high-affinity antibodies. The ELISPOT assay is reviewed in Current Protocols in Immunology, Unit 6.19 pages 6.19. 1-8.

The ELISPOT assay typically involves six steps: (1) coating a purified cytokine-specific antibody to a membrane-backed microtiter plate; (2) blocking the plate to prevent non-specific absorption of any other proteins; (3) incubating the cytokine-secreting cells with appropriate reagents; (4) removal of cells and reagents; (5) adding a labelled second anti-cytokine antibody; and (6) detecting the antibody-cytokine complex on the membrane.

Immune Responses

The immune response that is detected in vitro may be any response that is triggered by the at least three viral antigens of the present invention. The immune response may be mediated by any type of immune cell. In a particularly preferred embodiment, the immune response is mediated by peripheral blood mononuclear cells (PBMCs), which may comprise one or more types of immune cells selected from T-cells, natural killer (NK) cells and monocytes. Typically, the immune response is measured by assessing cytokine secretion, preferably by assessing interferon gamma (IFN-γ) secretion. Methods of measuring cytokine secretion are well known in the art. The immune response is preferably a T-cell response.

The immune response may occur in vitro. Preferably, the immune response is an in vitro CMI response. A CMI response is an immune response that does not involve antibodies. Instead, a CMI response may involve cytotoxic-T cell activation, increase in production of various cytokines and/or the release of various cytokines in response to an antigen. Methods for detecting in vitro CMI responses are known in the art and are described in detail above.

The method of the invention may detect the presence or absence of an immune response. The presence of an immune response to the at least three viral antigens according to the method of the present invention may indicate that the subject is immune competent. The absence of an immune response to the at least three viral antigens according to the method of the present invention may indicate that the subject has low immune competence.

Fragments

A fragment of a viral antigen according to the method of the present invention may be a sequence comprising five or more amino acids that is derived by truncation at the N-terminus and/or C-terminus of the parent sequence. For instance, the fragment may comprise about 5 or more, about 6 or more, about 7 or more, about 8 or more, about 9 or more, about 10 or more, about 11 or more, about 12 or more, about 13 or more, about 14 or more, about 15 or more, about 16 or more, about 17 or more, about 18 or more, about 19 or more, about 20 or more, about 21 or more, about 22 or more, about 23 or more, about 24 or more, about 25 or more, about 26 or more, or about 27 or more amino acids. The fragment may be from about 5 to about 27, from about 6 to about 26, from about 7 to about 25, from about 8 to about 24, from about 9 to about 23, from about 10 to about 22, from about 11 to about 21, from about 12 to about 20, from about 13 to about 19, from about 14 to about 18, from about 12 to about 18, from about 12 to about 15, from about 15 to about 18, from about 13 to about 17, from about 14 to about 16, from about 5 to about 10, from about 10 to about 15, from about 15 to about 20, from about 20 to about 25 or from about 10 to about 20 amino acids in length.

The fragments may be chemically derived from the parent protein, for example by proteolytic cleavage, or can be derived in an intellectual sense from the parent protein, for example by making use of the amino acid sequence of the parent protein and synthesising fragments based on the sequence. Fragments may be synthesised using methods well known in the art.

The term "fragment" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the fragment may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. One or more additional amino acid residues may also be added at the N-terminus and/or C-terminus of the fragment, for example to increase the stability of the fragment. Other examples of modifications include glycosylation and phosphorylation. Another potential modification is that hydrogens on the side chain amines of R or K may be replaced with methylene groups (—$NH_2$→—NH(Me) or —N(Me)$_2$).

Fragments of the at least three viral antigens according to the method of the present invention may also include variants of fragments that increase or decrease the fragments' half-life in vivo. Examples of variants capable of increasing the half-life of fragments according to the invention include peptoid analogues of the fragments, D-amino acid derivatives of the fragments, and peptide-peptoid hybrids. The fragment may also comprise D-amino acid forms of the fragment. The preparation of polypeptides using D-amino acids rather than L-amino acids greatly decreases any unwanted breakdown of such an agent by normal metabolic processes, decreasing the amounts of agent which needs to be administered, along with the frequency of its administration. D-amino acid forms of the parent protein may also be used.

The fragments according to the method of the present invention may be derived from splice variants of the parent proteins encoded by mRNA generated by alternative splicing of the primary transcripts encoding the parent protein chains. The fragments may also be derived from amino acid mutants, glycosylation variants and other covalent derivatives of the parent proteins which retain at least an MHC-binding or antibody-binding property of the parent protein. Exemplary derivatives include molecules wherein the fragments of the invention are covalently modified by substitution, chemical, enzymatic, or other appropriate means with a moiety other than a naturally occurring amino acid.

Fragment Pools

The method of the invention may comprise detecting in vitro an immune response to a pool of peptides, comprising one or more fragments. The pool of peptides may comprise fragments derived from viral antigens of a single virus, more than one virus, or from all different viruses. The pool of peptides may comprise fragments derived from viral antigens of the same virus and of different viruses. In a preferred aspect of the invention, one or more fragments are derived from at least three viral antigens, the at least three viral antigens derived from two viruses, preferably from three, four, five or six viruses. In a preferred embodiment, one or more fragments are derived from at least three viral antigens, the at least three viral antigens derived from one or more of the human adenovirus 3, the influenza virus, the Epstein Barr virus and the respiratory syncytial virus.

In a more preferred embodiment, the pool of peptides comprises one or more fragments of the one or more viral antigens selected from the hexon protein derived from the human adenovirus 3, the matrix protein 1 derived from the influenza virus, the nucleocapsid protein derived from the influenza virus, the BZLF protein derived from the Epstein Barr virus and the fusion glycoprotein G0 derived from the respiratory syncytial virus. The influenza virus can be any influenza strain. In a particularly preferred embodiment, the influenza virus is influenza strain H3N2.

In one embodiment of the invention, the pool of peptides comprises one or more fragments of the one or more viral antigens consisting of the hexon protein of human adenovirus 3, the fusion glycoprotein G0 of the respiratory syncytial virus and the nucleocapsid protein of the influenza virus.

In another embodiment of the invention, the pool of peptides comprises one or more fragments of the one or more viral antigens consisting of the hexon protein of human adenovirus 3, the matrix protein 1 of the influenza virus, the nucleocapsid protein of the influenza virus and the fusion glycoprotein G0 of the respiratory syncytial virus.

In a further embodiment of the invention, the pool of peptides comprises one or more fragments of the one or more viral antigens consisting of the hexon protein of human adenovirus 3, the trans-activator protein BZLF1 of the Epstein Barr virus and the fusion glycoprotein G0 of the respiratory syncytial virus.

In one embodiment of the invention, the pool of peptides comprises one or more fragments of the one or more viral antigens derived from Epstein Barr virus, wherein the viral antigens comprise BALF-4, BMLF-1, BRLF-1, BZLF-1 EBNA-1, EBNA-3A, EBNA-3B, EBNA-3C, EBNA-4, LMP-1 and/or LMP-2 proteins. In a particularly preferred embodiment, a pool of peptides comprising one or more fragments derived from EBV is provided, the pool of peptides including fragments derived from each of the BALF-4, BMLF-1, BRLF-1, BZLF-1 EBNA-1, EBNA-3A, EBNA-3B, EBNA-3C, EBNA-4, LMP-1 and/or LMP-2 proteins. Such a pool of EBV peptide fragments may be provided in combination with the hexon protein of human adenovirus 3, the matrix protein 1 of the influenza virus, the nucleocapsid protein of the influenza virus and the fusion glycoprotein G0 of the respiratory syncytial virus.

The pool may comprise one or more, two or more, three or more, four or more, five or more, six or more, seven or more, eight or more, nine of more, 10 or more, 15 or more, 20 or more, 25 or more, 50 or more, 75 or more, 100 or more, 200 or more, or 250 or more, fragments derived from the at least three viral antigens.

In one embodiment, the method of the invention comprises detecting in vitro an immune response to a pool of peptides comprising fragments. Preferably, the method comprises detecting in vitro an immune response to a pool of peptides wherein the pool of peptides comprises one or more fragments of the one or more viral antigens. Further preferably, the method comprises detecting in vitro an immune response to a pool of peptides wherein the pool of peptides comprises one or more fragments of each of the one or more viral antigens.

As set out below, the method may also comprise detecting in vitro an immune response to one or more protein fragment libraries.

Protein Fragment Libraries

In one embodiment, the fragments in a pool form a protein fragment library. A protein fragment library comprises a plurality of fragments derived from a parent protein, for the present invention, the hexon protein derived from the human adenovirus 3, the matrix protein 1 derived from the influenza virus, the nucleocapsid protein derived from the influenza virus, the BALF-4, BMLF-1, BRLF-1, BZLF-1 EBNA-1, EBNA-3A, EBNA-3B, EBNA-3C, EBNA-4, LMP-1 and LMP-2 proteins derived from the Epstein Barr virus and the fusion glycoprotein G0 derived from the respiratory syncytial virus, that together encompass at least 10%, such as at least 20%, at least 30%, at least 40%, at least 50%, at least 60%, at least 70%, at least 75%, at least 80%, at least 85%, at least 90%, at least 95%, at least 98%, at least 99%, or 100%, of the sequence of the parent protein. In the present invention, the fragments in a pool preferably form a protein fragment library encompassing at least 80% of the sequence of the protein from which the fragments are derived. More preferably, the fragments in a pool form a protein fragment library encompassing the entire sequence of the protein from which the fragments are derived.

The protein fragment library may comprise fragments that are capable of stimulating CD4+ and/or CD8+ T-cells. Preferably, the protein fragment library comprises fragments that are capable of stimulating both CD4+ and CD8+ T-cells. It is known in the art that the optimal fragment size for stimulation is different for CD4+ and CD8+ T-cells. Fragments consisting of about 9 amino acids (9mers) typically stimulate CD8+ T-cells only, and fragments consisting of about 20 amino acids (20mers) typically stimulate CD4+ T-cells only. Broadly speaking, this is because CD8+ T-cells tend to recognise their antigen based on its sequence, whereas CD4+ T-cells tend to recognise their antigen based on its higher-level structure. However, fragments consisting of about 15 amino acids (15mers) may stimulate both CD4+ and CD8+ T cells. Accordingly, the protein fragment library preferably comprises fragments that are about 15 amino acids, such as about 12 amino acids, about 13 amino acids, about 14 amino acids, about 15 amino acids, about 16 amino acids, about 17 amino acids or about 18 amino acids in length.

All of the fragments in a pool may be the same length. Alternatively, a pool may comprise fragments of different lengths. Fragment lengths are discussed above.

A protein fragment library may comprise fragments whose sequences overlap. Accordingly, each pool may comprise fragments whose sequences overlap. The sequences may overlap by one or more, such as two or more, three or more, four or more, five or more, six or more, seven or more, eight or more, nine or more, 10 or more, 11 or more, 12 or more, 13 or more, 14 or more, 15 or more, 16 or more, 17 or more, 18 or more, 19 or more, or 20 or more, amino acids. Preferably, the sequences overlap by 9 or more amino acids, such as 10 or more, 11 or more or 12 or more amino acids, as this maximises the number of fragments that comprise the 9mers capable of stimulating CD8+ T-cells. More preferably, the sequences overlap by 11 amino acids. All of the overlapping fragments in a pool may overlap by the same number of amino acids. Alternatively, a pool may comprise fragments whose sequences overlap by different numbers of amino acids.

The protein fragment library may comprise fragments of 12 to 18 (such as 12 to 15, 15 to 18, 13 to 17, or 14 to 16) amino acids in length that overlap by 9 to 12 (such as 9 to 11 or 10 to 12) amino acids. For instance, the protein fragment library may comprise fragments of (i) 14 amino acids in length that overlap by 9, 10, or 11 amino acids, (ii) 15 amino acids in length that overlap by 9, 10, or 11 amino acids, or (iii) 16 amino acids in length that overlap by 9, 10, or 11 amino acids. The protein fragment library preferably comprises fragments of 15 amino acids in length that overlap by 11 amino acids.

General properties of fragments are set out above.

The Epstein Barr virus pool may comprise 1, 2, 3, 4, 5, 6, 7, 8, 9, 10, 11, 12, 13, 14, 15, 16, 17, 18, 19, 20, 21, 22, 23, 24, 25 or 26 fragments derived from Epstein Barr virus peptides wherein overlapping fragments are not required. For example, the pool of peptides may comprise the peptide shown in Table 6.

Samples

The in vitro detection of an immune response to the at least three viral antigens of the present invention is performed using a sample obtained from the subject. In a preferred embodiment, the sample is a blood sample.

Subject

The method of the invention may be used to determine the immune competence of any suitable subject. The subject is generally a human subject.

Cells

In one embodiment, the method of the invention comprises conducting a cell-mediated immunoassay on a sample comprising immune cells, for example peripheral blood mononuclear cells, the method comprising detecting in vitro an immune response to a pool of peptides derived from at least three viral antigens. The pool of peptides may comprise one or more fragments of one or more of the viral antigens or one or more fragments of each of one of more viral antigens. The viral antigens may comprise one or more protein fragment libraries.

The sample is typically contacted with a sufficient amount of the at least three viral antigens to generate an immune response to the viral antigens. The sample may be contacted with the pool of peptides wherein the peptides or fragments have been combined prior to contacting the sample; or contacted with each viral antigen or fragment sequentially or concurrently using any combination of viral antigen or fragment. In a preferred embodiment, the sample is contacted with all the viral antigens concurrently, wherein viral antigens have been combined prior to contacting the sample.

The sample may be contacted with any amount of the at least three viral antigens, such as about 1 ng/ml, about 5 ng/ml, about 10 ng/ml, about 50 ng/ml, about 100 ng ml, about 500 ng/ml, about 1 µg/ml, about 5 µg/ml, about 10 µg/ml, about 50 µg/ml, about 100 µg ml, about 500 µg/ml, 1 mg/ml, about 5 mg/ml, about 10 mg/ml, about 50 mg/ml, about 100 mg ml, or about 500 mg/ml of the at least three viral antigens. The sample may be contacted with the at least three viral antigens concurrently or sequentially.

The immune cells may comprise one or more types of immune cells selected from T-cells, B-cells, dendritic cells, neutrophils, basophils, mast cells, eosinophils, innate lymphoid cells (ILCs), natural killer (NK) cells, monocytes, macrophages and thymocytes. The sample comprising immune cells may comprise a population of immune cells. The population may comprise all of these types of immune cells. The population may comprise peripheral blood mononuclear cells (PBMCs). A sample of PBMCs comprises T cells, B cells, NK cells and monocytes. The population of immune cells may comprise T-cells. In one embodiment, the population of immune cells comprises peripheral blood mononuclear cells.

The contacting of the cell sample with the at least three viral antigens may be carried out in any suitable volume. Typical volumes of the samples range from about 10 µl to about 1 ml, preferably from about 50 µl to about 500 µl, more preferably from about 100 µl to about 200 µl. Typically, the length of time for which the cells are contacted with the at least three viral antigens is from about 5 minutes to about 50 hours, for example from about 10 minutes to about 40 hours, from about 20 minutes to about 30 hours, from about 30 minutes to about 20 hours, from about 45 minutes to about 12 hours, from about 1 hour to about 6 hours, preferably from about 10 minutes to about 2 hours. The cells may be contacted with the antigens overnight.

The cells may be contacted with the antigen at any suitable temperature. The suitable temperature is typically in the same range as the normal body temperature of the human or animal from which the cells are derived. Typically, the incubation is carried out at a fixed temperature between about 4° C. and about 38° C., preferably from about 20° C. to about 38° C., more preferably at about 37° C.

The cells are typically present in wells. The cells are preferably present in the wells of a flat plate, which is preferably a membrane-backed plate. The samples are more preferably present in the wells of a standard 96 or 384 well plate. Such plates are commercially available Fisher scientific, VWR suppliers, Nunc, Starstedt or Falcon. The wells typically have a capacity of from about 25 µl to about 250 µl, from about 30 µl to about 200 µl, from about 40 µl to about 150 µl or from about 50 to 1000 µl The cells obtained from the subject can be cultured before being used in the methods. This allows equal numbers of adherent cells to be present in each sample being assayed. Alternatively, if the cells are immobilized or captured, the cells, such as fresh blood cells, can be counted before plating. Techniques for culturing cells are well known to a person skilled in the art. The cells are typically cultured under standard conditions of 37° C., 5% $CO_2$ in medium supplemented with serum.

The cells may be cultured in any suitable flask or vessel and then be transferred to wells. The cells are typically cultured in wells. The cells are preferably cultured in a flat plate comprising two or more wells, such as a standard 96 or 384 well plate. Incubating the cells with the marker typically involves replacing the culture medium in each well with a suitable solution comprising the marker. Suitable solutions are well known to a person skilled in the art.

Immune Responsiveness

As set out above, the method of the invention comprises detecting in vitro an immune response to at least three viral antigens. Detection of an immune response indicates that the subject is immune competent. The lack of detection (or absence of detection) of an immune response indicates that the subject is not immune responsive and has low immune competence. For example, an immune competent donor within the immune competency assay is one that has no spots in the negative control, greater than 20 spots in the positive control and produces specific IFN-γ spots in response to the immuno-competency assay (ICA) antigens.
Therapeutic Application The present invention provides for a method for determining immune competence of a subject, wherein the method comprises conducting a cell-mediated immunoassay (CMI) on a sample comprising immune cells, for example peripheral blood mononuclear cells (PBMCs) from the subject, the method comprising detecting in vitro an immune response to a pool of peptides, wherein the pool of peptides is derived from at least three viral antigens. The present method may be useful in the clinic to monitor the broad T cell responses of donors to the at least three viral antigens. This may be helpful to clinicians when assessing a patient's immune competence for several disease conditions including transplantation, cancer, autoimmune diseases, HIV and in vaccine trials.

EXAMPLES

Example 1—Selection of the Most Immunogenic Antigens

Healthy donor samples (31-167) were screened with 23 commercially available peptide pools in the ELISPOT assay. To identify the peptide pools that gave the best coverage of immunocompetent donors, an arbitrary 10 spot cut off was defined. The responses to each peptide pool were then assessed using the cut-off. Table 1 ranks the peptide pools based on the percentage of responsive donors.

TABLE 1

Ranking of peptide pools.

| Virus/Bacteria | Antigen | Abbreviation | Percentage Responsive (10 spot arbitrary cut off) | No of Peptides in the pool |
| --- | --- | --- | --- | --- |
| Human Adenovirus 3 | Hexon protein | Hexon | 85% (142/167 Donors) | 234 |
| Influenza | Matrix protein 1 (H3N2) | MP1 | 77% (61/79 Donors) | 61 |
| Epstein Barr Virus (EBV) | EBV | EBV | 73% (112/153 Donors) | 26 |
| Influenza | Nucleocapsid protein (H3N2) | NP | 62% (70/112 Donors) | 122 |
| Respiratory Syncytial Virus (RSV) | Fusion glycoprotein F0 | FGF0 | 50% (54/106 Donors) | 141 |
| Human Adenovirus 5 | Penton protein | Penton | 48% (81/167 Donors) | 140 |
| EBV | Epstein barr nuclear antigen 1 | EBNA1 | 48% (20/41 donors) | 158 |
| EBV | Epstein barr nuclear antigen 3a | EBNA-3a | 47% (72/153 Donors) | 234 |
| EBV | Trans-activator protein BZLF1 | BZLF1 | 45% (64/142 Donors) | 59 |
| Influenza | Influenza | INF | 40% (56/138 Donors) | 17 |
| RSV | Nucleocapsid protein N | NCPN | 29% (32/107 Donors) | 95 |
| RSV | Major surface glycoprotein | MSG | 26% (11/41 donors) | 72 |
| Influenza | Hemagglutinin of Influenza A (H1N1/Brisbane) | HA INF-bris | 25% (18/72 Donors) | 139 |
| Adenovirus | ADV | ADV | 19% (24/122 Donors) | 5 |
| EBV | Trans-activator protein BZLF1 | BZLF1 Protein | 17% (25/145 Donors) | N/A |
| Candida Albicans | Mannoprotein MP65 | MP65 | 14% (6/41 donors) | 92 |
| EBV | Epstein barr nuclear antigen-3A | EBNA-3a Protein | 13% (19/137 Donors) | N/A |
| RSV | RSV | RSV | 12% (5/39 Donors) | 28 |
| EBV | Latent membrane protein 2 | LMP2 | 9% (4/41 donors) | 122 |
| Influenza | Hemagglutinin of Influenza A (H1N1/California) | HA INF-ca | 8% (4/48 Donors) | 139 |
| EBV | DNA polymerase processivity factor BMRF1 | BMRF1 | 7% (3/41 donors) | 99 |
| Influenza | Matrix protein 2 | MP2 | 0% (0/34 Donors) | 22 |
| EBV | Secreted protein BARF1 | BARF1 | 0% (0/41 donors) | 53 |

This analysis allowed the selection of the 5 most responsive antigens (based on arbitrary 10 spot cut off)—Hexon, MP1, EBV, NP and FGF0.

Donors that were weak responders to the Hexon, MP1, EBV, NP and FGF0 (<10 spots) were assessed for responses to the remaining screened antigens. The BZLF1 antigen gave spot counts greater than 10 within these donors, so it was selected for further testing.

Example 2—Solubility

Custom peptide pools (Hexon, EBV, MP1, NP, FGF0 and BZLF1) were synthesized and supplied as lyophilised pools.

retical coverage of donors as if peptides from different antigens were combined into one pool. This was conducted by adding the spot counts for individual peptide pools (e.g. Donor 15, Hexon spot count=5, EBV spot count=26 NP spot count=5, Theoretical Mix 16 spot count=36). The percentage of donors within the 10-350 spot range was calculated for each mix. The results of this analysis are shown in table 2.

TABLE 2

Theoretical combination of peptide pools in an ELISPOT assay and resulting percentage coverage of donors. (n = 94-100)

| Theoretical Mix # | Theoretical Super Pools | | | | | Percentage of Donors within 10-350 spots | No of Donors tested |
|---|---|---|---|---|---|---|---|
| 1  | Hexon | MP1   | FGF0    |        |      | 97.9 | 94  |
| 2  | Hexon | FGF0  | NP      |        |      | 96.8 | 94  |
| 3  | Hexon | BZLF1 | MP1     | FGF0   |      | 96.8 | 94  |
| 4  | Hexon | BZLF1 | NP      | FGF0   |      | 94.7 | 94  |
| 5  | MP1   | NP    | FGF0    |        |      | 97.9 | 94  |
| 6  | Hexon | BZLF1 | MP1     |        |      | 98.0 | 100 |
| 7  | Hexon | NP    | BZLF1   |        |      | 96.0 | 100 |
| 8  | Hexon | MP1   | NP      | FGF0   |      | 97.9 | 94  |
| 9  | MP1   | NP    | BZLF1   | FGF0   |      | 95.7 | 94  |
| 10 | Hexon | BZLF1 | FGF0    |        |      | 93.6 | 94  |
| 11 | Hexon | MP1   | NP      | BZLF1  | FGF0 | 92.6 | 94  |
| 12 | BZLF1 | MP1   | NP      | FGF0   |      | 95.7 | 94  |
| 13 | Hexon | EBV   | FGF0    |        |      | 94.0 | 100 |
| 14 | BZLF1 | NP    | FGF0    |        |      | 92.6 | 94  |
| 15 | Hexon | EBV   | MP1     |        |      | 96.0 | 100 |
| 16 | Hexon | EBV   | NP      |        |      | 94.0 | 100 |
| 17 | Hexon | EBV   |         |        |      | 93.0 | 100 |
| 18 | EBV   | BZLF1 | MP1     | NP     |      | 89.0 | 100 |
| 19 | BZLF1 | MP1   | FGF0    |        |      | 93.6 | 94  |
| 20 | Hexon | EBV   | BZLF1   |        |      | 94.0 | 100 |
| 21 | Hexon | EBV   | MP1     | NP     |      | 90.0 | 100 |
| 22 | Hexon | EBV   | BZLF1   | EBNA-3a|      | 83.0 | 100 |
| 23 | EBV   | BZLF1 | EBNA-3a |        |      | 81.0 | 100 |
| 24 | Hexon |       |         |        |      | 87.0 | 100 |
| 25 | Hexon | EBV   | MP1     | NP     | FGF0 | 88.3 | 94  |
| 26 | Hexon | EBV   | BZLF1   | MP1    | NP   FGF0 | 79.8 | 94 |

The peptide pools were dissolved to a concentration of 625 µg/mL per peptide in the pool using Dimethyl Sulfoxide (DMSO).

Dissolution of all peptide pools was completed successfully. No solubility issues were observed.

Example 3—Assessment of the Stability of Individual Peptide Pools

The stability of each peptide pool at working concentration (3 µg/mL) was assessed using an accelerated stability study. Briefly: peptides pools at working concentration were stored at 37° C. for 8 weeks. The stressed peptide pools were then tested in comparison to freshly diluted peptide pools (control) in an ELISPOT assay. For each donor, 3 replicates were tested. The results from the studies are shown in FIG. 1.

Statistical analysis (Mann-Witney test) determined there was no statistical significant difference in the spot counts between the control and the peptides stored at 37° C. for 8 weeks.

Example 4—Combining Immunogenic Antigens

The data generated from the screening of peptide pools in an ELISPOT assay was re-assessed to determine the theo- The theoretical analysis identified:
- 10 mixes would have given responses to >95% of the donors assessed.
- Mixes 25 and 26 would theoretically give spot counts that are at the upper limit of what is accurately countable on an ELISPOT plate reader (400+ spots). This reduced the percentage of donors within the 10-350 spot count range.
- 13 mixes were selected for further testing in an ELISPOT assay (Table 3).

TABLE 3

Selected mixes of peptide pools for the immuno-competency assay (ICA).

| ICA Mix | Antigens in Mix | | | | No of Peptides |
|---|---|---|---|---|---|
| 1  | Hexon | MP1   | FGF0  |      | 436 |
| 2  | Hexon | FGF0  | NP    |      | 497 |
| 3  | Hexon | BZLF1 | MP1   | FGF0 | 495 |
| 4  | Hexon | BZLF1 | NP    | FGF0 | 556 |
| 5  | MP1   | NP    | FGF0  |      | 324 |
| 6  | Hexon | MP1   | NP    | FGF0 | 558 |
| 7  | MP1   | NP    | BZLF1 | FGF0 | 383 |
| 8  | Hexon | NP    | BZLF1 |      | 415 |
| 9  | Hexon | BZLF1 | FGF0  |      | 434 |
| 10 | Hexon | BZLF1 | MP1   |      | 354 |

TABLE 3-continued

Selected mixes of peptide pools for the immuno-competency assay (ICA).

| ICA Mix | Antigens in Mix | | | | | No of Peptides |
|---|---|---|---|---|---|---|
| 11 | EBV | BZLF1 | MP1 | NP | | 268 |
| 12 | Hexon | EBV | MP1 | NP | FGF0 | 584 |
| 13 | Hexon | EBV | BZLF1 | MP1 | NP | FGF0 | 643 |

Figure 2:
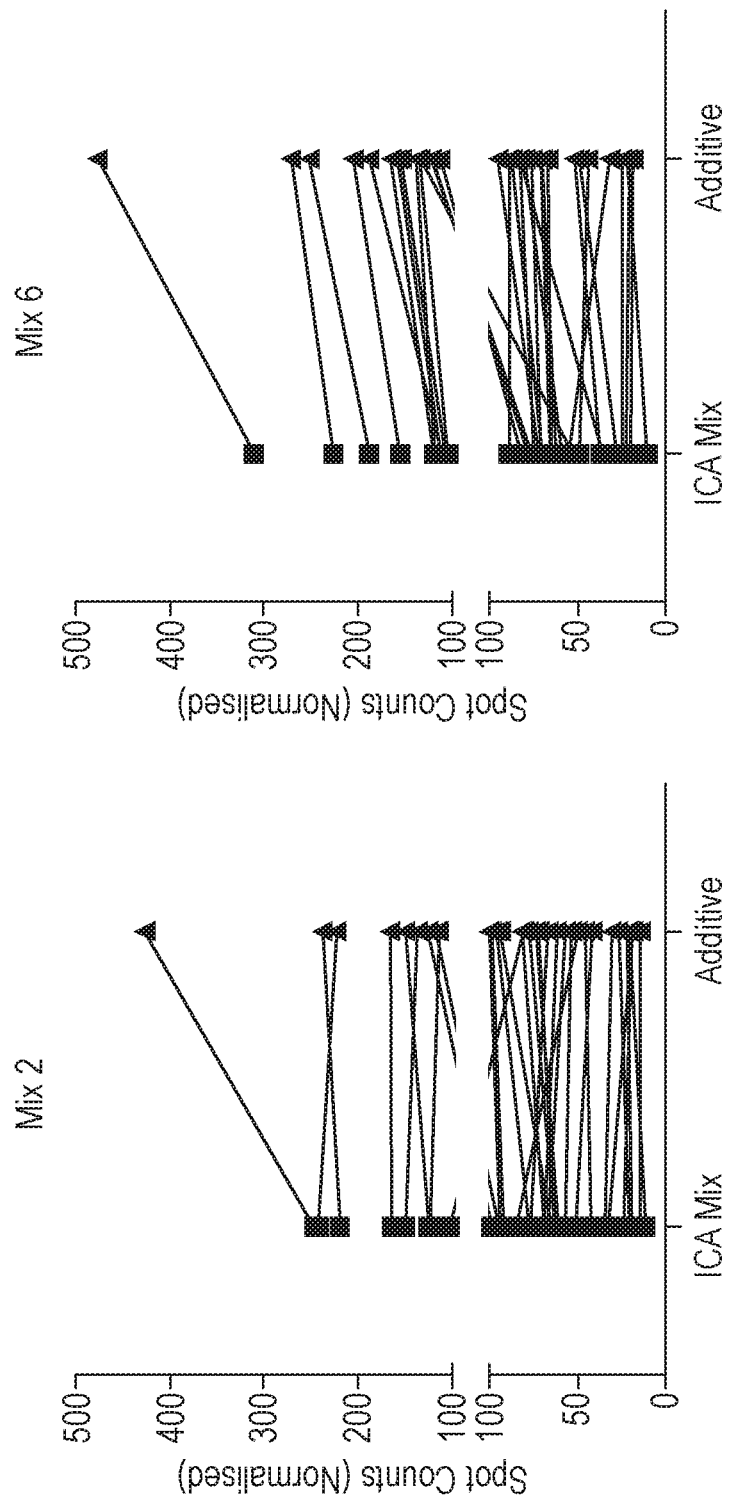
FIG. 2. Example graphs for combined peptide pools (ICA Mix) vs individual peptide pools summed (Additive) in an ELISPOT assay.

To confirm that the predicted performance of the combined peptide pools would be achieved, the peptide pools were tested individually and in mixes in an ELISPOT assay with 32 donors. Obtained spot counts for the mixes were compared to the additive spot count from the individual antigens (e.g. Donor 9743, Hexon spot count=5, MP1 spot count=10 FGF0 spot count=6, Mix 1 spot count=28). The results of this comparison are shown in FIG. 2.

Statistical analysis (Mann-Witney test) determined there was no significant statistical difference between the additive spot counts of the individual peptide pools and the combined ICA mix.

Example 5—Preparation of ICA Mixes

The dissolved peptide pools (625 µg/mL per peptide in the pool) were combined into the immuno-competency assay (ICA) mixes. No issues were observed during preparation.

Example 6—Ethnicity

Figure 3:
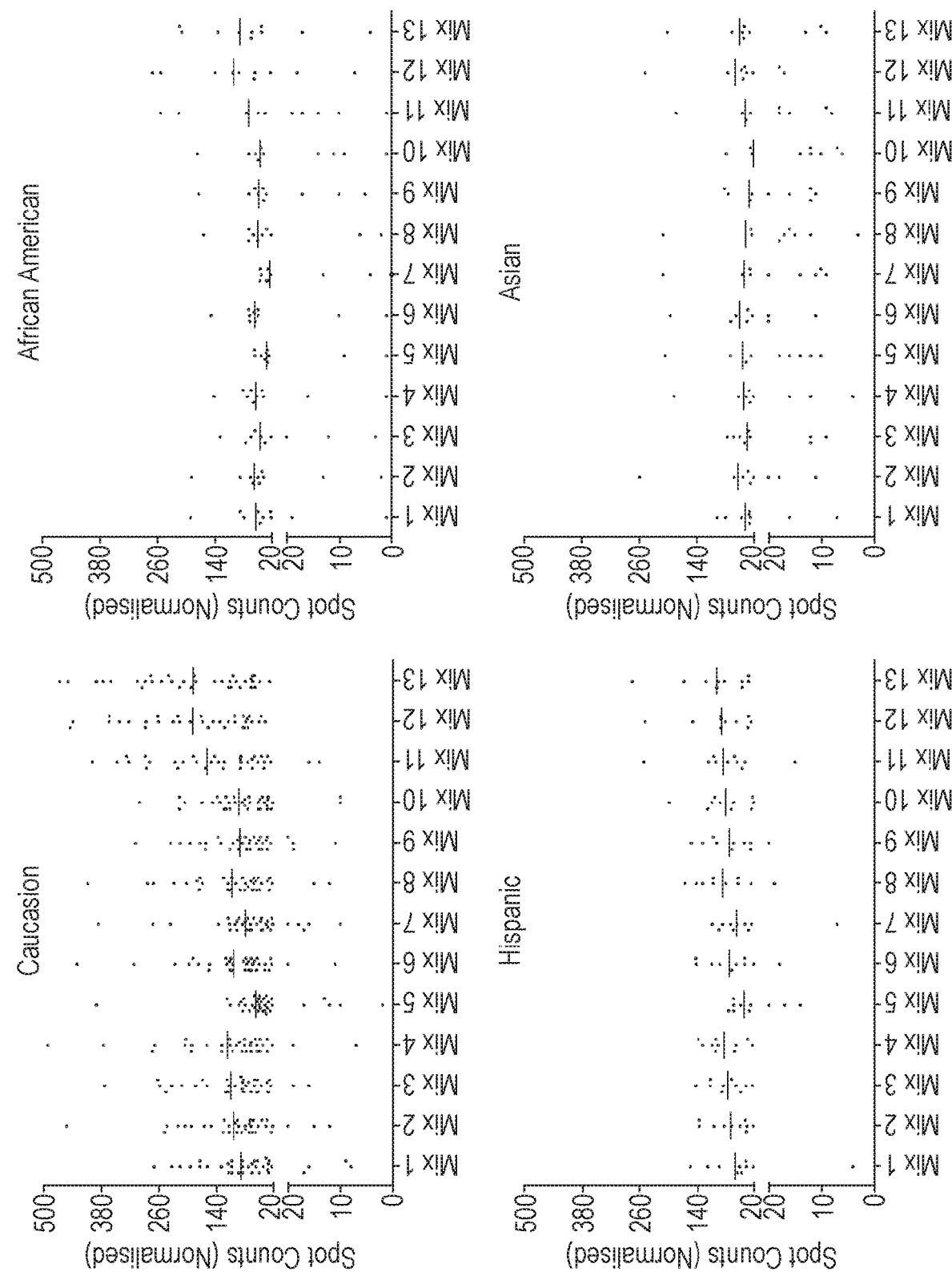
FIG. 3. Testing donors of varied ethnicities in an ELISPOT assay.

The 13 selected ICA mixes were tested in an ELISPOT assay with blood samples collected from 35 Caucasians, 10 African Americans, 10 Hispanic and 9 Asian donors. The results of this testing are shown in FIG. 3.

A 10 spot cut off was used to determine the number of responsive donors (Table 4).

4 of the 13 mixes (ICA mixes 2, 6, 9 and 12) were responsive in ≥90% of the donors tested regardless of ethnicity, based on a 10 spot cut off.

Example 7—Fluctuation of Responses Over Time to ICA Mixes

To determine the natural variation of response induced by the ICA mixes, 6 immunocompetent blood donors were tested at time points: day 0, 3, 7, 14, 28, 56, and 84 with the ICA mixes in an ELISPOT assay.

FIG. 4 shows variation of response over a short period of time (7 days) and longer period of time (84 days) for two example mixes.

Statistical analysis was performed by BioBridges.
Briefly: The coefficient of variation (% CV) was calculated for the individual mixes with each donor using data from all time points. Following this, the % CV values for each mix from the 6 donors were grouped and a mean calculated. The mean of these % CV's is a measure of the variance of spot counts using ICA mixes in an ELISPOT assay, see Table 4 for summary.

TABLE 5

Statistical analysis of the natural variation of immunocompetent responses to ICA mixes in the ELISPOT assay. (n = 6)

| ICA Mix | Variation (Over 7 days) | Variation (Over 84 days) |
|---|---|---|
| Mix 1 | 20% | 26% |
| Mix 2 | 16% | 21% |
| Mix 3 | 13% | 23% |
| Mix 4 | 11% | 18% |
| Mix 5 | 22% | 25% |
| Mix 6 | 18% | 23% |
| Mix 7 | 24% | 31% |
| Mix 8 | 18% | 25% |
| Mix 9 | 19% | 25% |
| Mix 10 | 21% | 24% |
| Mix 11 | 27% | 34% |
| Mix 12 | 21% | 23% |
| Mix 13 | 25% | 24% |

TABLE 4

Percentage of donors responsive to ICA mixes based on an arbitrary 10 spot cut off.

Percentage Responsive Donors (Based on an arbitrary 10 spot cut off)

| | Mix 1 | Mix 2 | Mix 3 | Mix 4 | Mix 5 | Mix 6 | Mix 7 | Mix 8 | Mix 9 | Mix 10 | Mix 11 | Mix 12 | Mix 13 |
|---|---|---|---|---|---|---|---|---|---|---|---|---|---|
| Caucasian (n = 35) | 94% | 100% | 100% | 97% | 97% | 100% | 100% | 100% | 100% | 100% | 100% | 100% | 100% |
| African American (n = 10) | 90% | 90% | 90% | 90% | 80% | 90% | 80% | 80% | 90% | 80% | 90% | 90% | 90% |
| Hispanic (n = 10) | 90% | 100% | 100% | 100% | 100% | 100% | 90% | 100% | 100% | 100% | 100% | 100% | 100% |
| Asian (n = 9) | 89% | 100% | 89% | 89% | 100% | 100% | 89% | 89% | 100% | 78% | 78% | 100% | 89% |

TABLE 6

EBV Pool

| | Peptide Sequence | Parent Protein | Location | Prot ID | SEQ ID Number |
|---|---|---|---|---|---|
| 1 | FLDKGTYTL | BALF-4 | 276-284 | P03188 | SEQ ID NO: 1 |
| 2 | GLCTLVAML | BMLF-1 | 259-267 | Q04360 | SEQ ID NO: 2 |
| 3 | DYCNVLNKEF | BRLF1 | 28-37 | P03209 | SEQ ID NO: 3 |
| 4 | ATIGTAMYK | BRLF1 | 134-142 | P03209 | SEQ ID NO: 4 |
| 5 | RVRAYTYSK | BRLF-1 | 148-156 | P03209 | SEQ ID NO: 5 |
| 6 | RAKFKQLL | BZLF-1 | 190-197 | P03206 | SEQ ID NO: 6 |
| 7 | EPLPQGQLTAY | BZLF-1 | 54-64 | P03206 | SEQ ID NO: 7 |
| 8 | HPVGEADYFEY | EBNA-1 | 407-417 | P03211 | SEQ ID NO: 8 |
| 9 | QAKWRLQTL | EBNA-3A | 158-166 | P12977 | SEQ ID NO: 9 |
| 10 | FLRGRAYGL | EBNA-3A | 193-201 | P12977 | SEQ ID NO: 10 |
| 11 | RPPIFIRRL | EBNA-3A | 247-255 | P12977 | SEQ ID NO: 11 |
| 12 | YPLEIEQHGM | EBNA-3A | 458-466 | P12977 | SEQ ID NO: 12 |
| 13 | RLRAEAQVK | EBNA-3A | 603-611 | P12977 | SEQ ID NO: 13 |
| 14 | AVFDRKSDAK | EBNA-3B | 399-408 | I1YP20 | SEQ ID NO: 14 |
| 15 | RRIYDLIEL | EBNA-3C | 79-87 | Q69140 | SEQ ID NO: 15 |
| 16 | EENLLDFVRF | EBNA-3C | 102-111 | Q69140 | SEQ ID NO: 16 |
| 17 | QPRAPIRPI | EBNA-3C | 881-889 | Q69140 | SEQ ID NO: 17 |
| 18 | IVTDFSVIK | EBNA-4 | 416-424 | P03203 | SEQ ID NO: 18 |
| 19 | YLLEMLWRL | LMP-1 | 125-133 | P03230 | SEQ ID NO: 19 |
| 20 | PYLFWLAAI | LMP2 | 131-139 | P13285 | SEQ ID NO: 20 |
| 21 | IEDPPFNSL | LMP2 | 200-208 | P13285 | SEQ ID NO: 21 |
| 22 | SSCSSCPLSK | LMP-2 | 340-349 | P13285 | SEQ ID NO: 22 |
| 23 | FLYALALLL | LMP-2 | 356-364 | P13285 | SEQ ID NO: 23 |
| 24 | TYGPVFMCL | LMP-2 | 419-427 | P13285 | SEQ ID NO: 24 |
| 25 | TYGPVFMSL | LMP2 | 419-427 | P13285 | SEQ ID NO: 25 |
| 26 | CLGGLLTMV | LMP-2 | 426-434 | P13285 | SEQ ID NO: 26 |

Epstein Barr Virus, Transactivator protein BZLF1 Prot ID: P03206
SEQ ID NO: 27
MMDPNSTSEDVKFTPDPYQVPFVQAFDQATRVYQDLGGPSQAPLPCVLWPVLPEPLPQGQ

LTAYHVSTAPTGSWFSAPQPAPENAYQAYAAPQLFPVSDITQNQQTNQAGGEAPQPGDNS

TVQTAAAVVFACPGANQGQQLADIGVPQPAPVAAPARRTRKPQQPESLEECDSELEIKRY

KNRVASRKCRAKFKQLLQHYREVAAAKSSENDRLRLLLKQMCPSLDVDSIIPRTPDVLHE

DLLNF

Human Adenovirus 3, Hexon Protein Prot ID: P36849
>sp|P36849|CAPSH_ADE03 Hexon protein OS = Human adenovirus B serotype 3
GN = L3 PE = 2 SV = 2
SEQ ID NO: 28
MATPSMMPQWAYMHIAGQDASGYLSPGLVQFARATDTYFSMGNKFRNPTVAPTHDVTTDR

SQRLMLRFVPVDREDNTYSYKVRYTLAVGDNRVLDMASTFFDIRGVLDRGPSFKPYSGTA

-continued

YNSLAPKGAPNTSQWIVTTNGDNAVTTTTNTFGIASMKGGNITKEGLQIGKDITTTEGEE

KPIYADKTYQPEPQVGEESWTDTDGTNEKFGGRALKPATNMKPCYGSFARPTNIKGGQAK

NRKVKPTTEGGVETEEPDIDMEFFDGRDAVAGALAPEIVLYTENVNLETPDSHVVYKPET

SNNSHANLGQQAMPNRPNYIGFRDNFVGLMYYNSTGNMGVLAGQASQLNAVVDLQDRNTE

LSYQULDSLGDRTRYFSMWNQAVDSYDPDVRIIENHGIEDELPNYCFPLNGIGPGHTYQ

GIKVKTDDTNGWEKDANVAPANEITIGNNLAMEINIQANLWRSFLYSNVALYLPDVYKYT

PPNITLPTNTNTYEYMNGRVVSPSLVDSYINIGARWSLDPMDNVNPFNHHRNAGLRYRSM

LLGNGRYVPFHIQVPQKFFAVKNLLLLPGSYTYEWNFRKDVNMVLQSSLGNDLRTDGATI

SFTSINLYATFFPMAHNTASTLEAMLRNDTNDQSFNDYLSAANMLYPIPANATNIPISIP

SRNWAAFRGWSFTRLKTKETPSLGSGFDPYFVYSGSIPYLDGTFYLNHTFKKVAIMFDSS

VSWPGNDRLLSPNEFEIKRTVDGEGYNVAQCNMTKDWFLVQMLANYNIGYQGFYIPEGYK

DRMYSFFRNFQPMSRQVVDEVNYTDYKAVTLPYQHNNSGFVGYLAPTMRQGEPYPANYPY

PLIGTTAVKSVTQKKFLCDRTMWRIPFSSNFMSMGALTDLGQNMLYANSAHALDMTFEVD

PMDEPTLLYLLFEVFDVVRVHQPHRGVIEAVYLRTPFSAGNATT

Influenza A (H3N2) Virus, Nucleoprotein ProtID: I6LFN1
>tr|I6LFN1|I6LFN1_9INFA Nucleoprotein OS = Influenza A virus
(A/Nanchang/A2/1994(H3N2)) GN = NP PE = 3 SV = 1

SEQ ID NO: 29

MASQGTKRSYEQMETDGERQNATEIRASVGKMIDGIGRFYIQMCTELKLSDYEGRLIQNS

LTIERMVLSAFDERRNRYLEEHPSAGKDPKKTGGPIYKRVDGRWMRELVLYDKEEIRRIW

RQANNGDDATAGLTHMMIWHSNLNDTTYQRTRALVRTGMDPRMCSLMQGSTLPRRSGAAG

AAVKGIGTMVMELIRMIKRGINDRNFWRGENGRKTRSAYERMCNILKGKFQTAAQRAMMD

QVRESRNPGNAEIEDLIFSARSALILRGSVAHKSCLPACVYGPAVSSGYNFEKEGYSLVG

IDPFKLLQNSQVYSLIRPNENPAHKSQLVWMACHSAAFEDLRLLSFIRGTKVSPRGKLST

RGVQIASNENMDNMESSTLELRSRYWAIRTRSGGNTNQQRASAGQISVQPTFSVQRNLPF

EKSTVMAAFTGNTEGRTSDMRAEIIRMMEGAKPEEVSFRGRGVFELSDEKATNPIVPSFD

MSNEGSYFFGDNAEEYDN

Respiratory Syncytial Virus, Fusion GlycoProtein F0 ProtID: O36634
>sp|O36634|FUS_HRSVB Fusion glycoprotein F0 OS = Human respiratory
syncytial virus B (strain B1) GN = F PE = 1 SV = 1

SEQ ID NO: 30

MELLIHRLSAIFLTLAINALYLTSSQNITEEFYQSTCSAVSRGYFSALRTGWYTSVITIE

LSNIKETKCNGTDTKVKLIKQELDKYKNAVTELQLLMQNTPAANNRARREAPQYMNYTIN

TTKNLNVSISKKRKRRFLGFLLGVGSAIASGIAVSKVLHLEGEVNKIKNALLSTNKAVVS

LSNGVSVLTSKVLDLKNYINNQLLPIVNQQSCRISNIETVIEFQQKNSRLLEINREFSVN

AGVTTPLSTYMLTNSELLSLINDMPITNDQKKLMSSNVQIVRQQSYSIMSIIKEEVLAYV

VQLPIYGVIDTPCWKLHTSPLCTTNIKEGSNICLTRTDRGWYCDNAGSVSFFPQADTCKV

QSNRVFCDTMNSLTLPSEVSLCNTDIFNSKYDCKIMTSKTDISSSVITSLGAIVSCYGKT

KCTASNKNRGIIKTFSNGCDYVSNKGVDTVSVGNTLYYVNKLEGKNLYVKGEPIINYYDP

LVFPSDEFDASISQVNEKINQSLAFIRRSDELLHNVNTGKSTTNIMITTIIIVIIVVLLS

LIAIGLLLYCKAKNTPVTLSKDQLSGINNIAFSK

Influenza A virus (H3N2). Matrix Protein 1. ProtID: Q67157
>sp|Q67157|M1_I68A0 Matrix protein 1 OS = Influenza A virus
(strain A/Aichi/2/1968 H3N2) GN = M PE = 3 SV = 1

SEQ ID NO: 31

MSLLTEVETYVLSIVPSGPLKAEIAQRLEDVFAGKNTDLEALMEWLKTRPILSPLTKGIL

GFVFTLTCPSERGLQRRRFVQNALNGNGDPNNMDRAVKLYRKLKREITFHGAKEIALSYS

AGALASCMGLIYNRMGAVTTEVAFGLVCATCEQIADSQHRSHRQMVTTTNPLIRHENRMV

LASTTAKAMEQMAGSSEQAAEAMEVASQARQMVQAMRAIGTHPRSSAGLKDDLLENLQAY

QKRMGVQMQRFK

---

The invention claimed is:

1. A method for determining the cell mediated immune competence of a subject, the method comprising conducting a cell-mediated immunoassay (CMI) on a sample comprising immune cells from the subject, and detecting in vitro an immune response to a pool of peptides, wherein the pool of peptides is derived from at least three but not more than five viral antigens selected from hexon protein of human adenovirus 3, matrix protein 1 of influenza virus, BZLF-1 protein of Epstein Barr virus, nucleocapsid protein of influenza virus, and fusion glycoprotein G0 of respiratory syncytial virus.

2. The method of claim 1, wherein the immune cells are peripheral blood mononuclear cells (PBMCs).

3. The method of claim 1, wherein the immune cells are T cells.

4. The method of claim 1, wherein the pool of peptides is derived from at least four viral antigens.

5. The method of claim 1, wherein the pool of peptides is derived from three, four or five viral antigens.

6. The method of claim 1, wherein the viral antigens consist of a hexon protein of human adenovirus 3, a fusion glycoprotein G0 of respiratory syncytial virus and a nucleocapsid protein of influenza virus.

7. The method of claim 1, wherein the viral antigens consist of a hexon protein of human adenovirus 3, a matrix protein 1 of influenza virus, a nucleocapsid protein of influenza virus and a fusion glycoprotein G0 of respiratory syncytial virus.

8. The method of claim 1, wherein the viral antigens consist of a hexon protein of human adenovirus 3, a transactivator protein BZLF1 of Epstein Barr virus and a fusion glycoprotein G0 of respiratory syncytial virus.

9. The method of claim 1, wherein the pool of peptides comprise one or more fragments derived from one or more viral antigens selected from hexon protein of human adenovirus 3, matrix protein 1 of influenza virus, BZLF-1 protein of Epstein Barr virus, nucleocapsid protein of influenza virus, and fusion glycoprotein G0 of respiratory syncytial virus.

10. The method of claim 1, wherein the pool of peptides comprise one or more fragments derived from each of the one or more viral antigens selected from hexon protein of human adenovirus 3, matrix protein 1 of influenza virus, BZLF-1 protein of Epstein Barr virus, nucleocapsid protein of influenza virus, and fusion glycoprotein G0 of respiratory syncytial virus.

11. The method of claim 9, wherein the fragments form a protein fragment library encompassing at least 80% of the sequence of the viral antigen from which the fragments are derived.

12. The method of claim 11, wherein the fragments form a protein fragment library encompassing the entire sequence of the viral antigen from which the fragments are derived.

13. The method of claim 9, wherein the fragments have overlapping sequences.

14. The method of claim 13, wherein the sequences overlap by 11 amino acids.

15. The method of claim 10, wherein the fragments are 15 amino acids in length.

16. The method of claim 1, wherein the influenza virus is influenza strain H3N2.

* * * * *

UNITED STATES PATENT AND TRADEMARK OFFICE
CERTIFICATE OF CORRECTION

PATENT NO. : 11,112,401 B2  
APPLICATION NO. : 16/086811  
DATED : September 7, 2021  
INVENTOR(S) : Scott Tasker It is certified that error appears in the above-identified patent and that said Letters Patent is hereby corrected as shown below:

In the Claims

In Claim 15, Column 42, Line 57, replace "The method of claim 10" with --The method of claim 9--.

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*